(12) United States Patent
Dittrich

(10) Patent No.: US 7,714,015 B2
(45) Date of Patent: *May 11, 2010

(54) METHOD AND COMPOSITION FOR TREATING SUNBURNED SKIN

(75) Inventor: Wayne Dittrich, Marlette, MI (US)

(73) Assignee: Lil Brat Pharmaceuticals of Marlette, MI, Marlette, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/636,404

(22) Filed: Aug. 7, 2003

(65) Prior Publication Data

US 2005/0031555 A1 Feb. 10, 2005

(51) Int. Cl.
*A01N 43/36* (2006.01)
*C07D 293/00* (2006.01)

(52) U.S. Cl. .................... 514/408; 548/100; 424/401
(58) Field of Classification Search ................. 424/401, 424/59; 574/420; 514/408

See application file for complete search history.

(56) References Cited

U.S. PATENT DOCUMENTS

| | | | |
|---|---|---|---|
| 3,629,412 A | 12/1971 | Silber et al. | |
| 4,088,754 A * | 5/1978 | Monafo | 424/617 |
| 4,309,414 A | 1/1982 | Inagi et al. | |
| 4,384,000 A * | 5/1983 | Lanier | 514/330 |
| 4,518,608 A | 5/1985 | Kahan | |
| 4,540,572 A | 9/1985 | Seth | |
| 4,732,755 A * | 3/1988 | Grana | 424/78.06 |
| 4,847,283 A | 7/1989 | Harendza-Harinxma | |
| 4,933,362 A | 6/1990 | Loomstein | |
| 4,954,487 A * | 9/1990 | Cooper et al. | 514/159 |
| 5,558,914 A | 9/1996 | Cohen et al. | |
| 5,674,912 A * | 10/1997 | Martin | 514/724 |
| 5,705,196 A * | 1/1998 | Galan Valdivia et al. | 424/497 |
| 5,725,874 A * | 3/1998 | Oda et al. | 424/443 |
| 5,807,569 A | 9/1998 | Davis et al. | |
| 6,221,377 B1 * | 4/2001 | Meyer | 424/434 |
| 6,274,627 B1 | 8/2001 | Lai et al. | |
| 6,337,320 B1 | 1/2002 | Hersh et al. | |
| 6,399,651 B1 * | 6/2002 | Parks | 514/453 |
| 2001/0055599 A1 | 12/2001 | Drzewiecki et al. | |
| 2002/0143047 A1 | 10/2002 | Galer et al. | |

FOREIGN PATENT DOCUMENTS

| | | | |
|---|---|---|---|
| JP | 57165313 A | * | 10/1982 |
| JP | 60105613 A | * | 6/1985 |
| WO | WO 99/45921 A1 | * | 9/1999 |

OTHER PUBLICATIONS

Sekura Snyder, D.: "Cutaneous effect of topical indomethacin, an inhibitor of prostaglandin synthesis, on UV-damaged skin" The Journal of Investigative Dermatology, vol. 64, No. 5, 1975, p. 322-325.
Allen, L. V. Jr. and Stiles, M. L.: "Topical indomethacin" US Pharmacist, vol. 13, No. 12, Dec. 1988, p. 52-53.
Cho, M.K. et al.:"The effect of topical indomethacin and topical corticosteroid on UVB induced erythema" Annals of Dermatology, vol. 7, No. 2, Apr. 1995, p. 144-149.
Schwarz, T. et al.: "Photoprotective effect of topical indomethacin-an experimental study" Dermatologica, vol. 171, 1985. p. 450-458.
Kimura, T. and Doi, K.: "Effects of indomethacin on sunburn and suntan reactions in hairless descendent of Mexican hairless dogs" Histol Histopathol, vol. 13, 1998, p. 29-36.

* cited by examiner

*Primary Examiner*—Sreeni Padmanabhan
*Assistant Examiner*—Layla Soroush
(74) *Attorney, Agent, or Firm*—Young Basile P.C.

(57) ABSTRACT

The present invention relates to a method and composition for treating sunburned skin. The present invention provides a method and composition for applying a mixture of indomethacin and moisturizing lotion topically to sunburned skin. The composition includes a mixture having substantially 100 milligrams of indomethacin per 30 cc of moisturizing lotion. The moisturizing lotion is marketed under the trade name Cetaphil® and includes the following ingredients: purified water, glycerin, hydrogenated polyisobutene, cetearyl alcohol (and) ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium hydroxide, and citric acid. It is theorized that the Cetaphil® provides certain pH and viscosity levels which allow for the stabilization and solubilation of the indomethacin within the Cetaphil®.

2 Claims, No Drawings

METHOD AND COMPOSITION FOR TREATING SUNBURNED SKIN

FIELD OF THE INVENTION

The present invention relates to a method and composition for treating sunburned skin, and more particularly, a method and composition for a topical application of an indomethacin and moisturizing lotion formulation for the treatment of sunburned skin.

BACKGROUND OF THE INVENTION

Although there has been substantial effort in recent years to reduce or eliminate the risk of sunburn (erythema) produced by certain wavelengths in the ultraviolet (UV) region of the spectrum, there are still circumstances wherein skin becomes exposed to UV radiation. Such exposure may, in some cases, cause sunburn. Such sunburn may cause irritation and pain to the skin thereby leading to the need for having the sunburn treated.

A number of prior art formulations have been developed for the treatment of sunburned skin. However, such treatments have certain disadvantages. For example, sunburn treatments that provide a spray mist or a petroleum-based composition to the sunburned area do not produce a sufficiently large heat transference effect to remove heat from the sunburned area. Furthermore, petroleum-based compositions tend to produce a residue that needs to be subsequently cleansed from the tender and sensitive area of the sunburned skin. Such cleansing tends to cause further discomfort and irritation to the affected skin.

Preferably, a treatment for sunburn would satisfy several objectives simultaneously. The main objective for the treatment of sunburn would be to relieve pain, eliminate the source of heat, stop the burn progression, and, if necessary, help prevent infection. Thus, a useful treatment for sunburn preferably provides immediate relief from pain while also helping to promote healing. It would be desirable to have a formulation for treatment of sunburn to be combined in a reasonably convenient and cost-effective process wherein the prepared composition would remain stable during storage. Such a sunburn formulation should provide the relief and healing effects sought without producing an uncomfortable, sticky sensation and without soiling or sticking to one's clothing. In addition, the sunburn formulation should preferably not produce a residue that must be subsequently washed or removed from the sensitive sunburned area.

Since a sunburn is an inflammatory disorder, sunburn has been treated in the past with anti-inflammatory drugs. One of the most effective therapeutics is indomethacin [1-(p-chlorobenzoyl)-5-methoxy-2-methylindole-3-acetic acid], a non-steroid chemical compound that has been widely recognized for its outstanding anti-inflammatory, anti-pyretic, and analgesic properties. However, indomethacin can become unstable when mixed with certain carriers for topical applications, and therefore, oral administration is sometimes the preferred method of administration.

Oral administration of indomethacin has previously been reported as effective in relieving pain, reducing fever, and providing increased mobility in patients with inflammatory disorders, including those of a rheumatic nature. When orally administered, the drug behaves as a systemic medicine that passes into the bloodstream for general distribution in the body. As in the case with numerous other drugs, not every one can satisfactorily accept this drug by the oral mode of administration, particularly over extending periods of therapy. In addition, oral administration does not provide for the direct and concentrated application of indomethacin on an affected area, such as an area of sunburned skin.

It would be desirable to provide a non-oral method of administering indomethacin for the treatment of sunburned skin. In addition, it would be desirable to provide a carrier vehicle for the topical application of indomethacin whereby local treatment of inflammation is achieved to an area of sunburned skin. It would also be desirable to provide a carrier for indomethacin that provided a topical application which utilized a reasonably convenient and cost-effective process that remained stable during storage.

SUMMARY OF THE INVENTION

The present invention relates to a method and composition for treating sunburned skin. The method of the present invention comprises the steps of providing an indomethacin and a moisturizing lotion. The indomethacin and moisturizing lotion are combined to form a mixture for applying the mixture topically to sunburned skin to relieve the symptoms associated with sunburned skin. The mixture is applied one to two times daily to the sunburned skin.

The composition of the present invention provides a mixture of indomethacin and moisturizing lotion. The mixture provides substantially 100 milligrams of indomethacin per substantially 30 cc of moisturizing lotion. The moisturizing lotion may contain emollients and humectants. The moisturizing lotion may also contain purified water, glycerin, hydrogenated polyisobutene, cetearyl alcohol (and) ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium hydroxide, and citric acid. The moisturizing lotion may be marketed under the trade name Cetaphil®.

DESCRIPTION OF THE PREFERRED EMBODIMENT

The present invention will now be described in detail with reference to the disclosed embodiment.

The present invention provides a method and composition for treating sunburned skin of a human being. The composition includes a mixture of indomethacin and a moisturizing lotion. The composition is applied topically to the sunburned skin to provide highly effective relief of the symptoms associated with sunburned skin, including the local inflammation caused by the sunburn. It is believed that the skin, with the presence of the topical formulation, acts as a reservoir, absorbing large amounts of the indomethacin and slowly releasing the indomethacin into the skin and to other tissues. The skin may actually act as a depot or reservoir for the indomethacin. It is believed that the indomethacin is stabilized and solubilized by the moisturizing lotion wherein the moisturizing lotion enhances the absorption of the indomethacin through the skin and accordingly permits the drug to be employed topically for inflammation of the sunburned skin. Experimental results with the indomethacin have shown that far better results are achieved in relieving sunburned skin than other anti-inflammatory drugs, such as Motrin® and Tolectin®.

Experimental results have also shown that the use of the moisturizing lotion, marketed under the trademark Cetaphil® by Galderma Laboratories, Inc., Fort Worth, Tex. 76133, performs well in stabilizing and solubilizing the indomethacin in creating the composition for treating sunburned skin. It is theorized that Cetaphil® provides the appropriate pH and viscosity levels to effectively stabilize and solubilize the indomethacin within the moisturizing lotion. The Cetaphil® provides emollients and humectants which are clinically proven to bind water to the skin and prevent moisture loss. The ingredients of Cetaphil® include purified water, glycerin, hydrogenated polyisobutene, cetearyl alcohol (and) ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium hydroxide, and citric acid.

To provide an effective mixture of the indomethacin and the Cetaphil®, experimentation has found that a proper mixture having substantially 100 milligrams of indomethacin per 30 cc of Cetaphil® lotion will act as an effective treatment for sunburned skin. This mixture level allows the Cetaphil® to act as a proper stabilizer and solubilizer for the indomethacin. A stronger or weaker indomethacin mixture may be created depending on the treatment. However, experimentation has shown that the above-noted mixture remains an effective mixture for the treatment of sunburned skin.

In use, the disclosed amounts of indomethacin and Cetaphil® are mixed to create the appropriate composition. The composition is applied to the sunburned areas thereby providing almost immediate relief of the pain and discomfort associated with sunburn. The moisturizing lotion provides moisture and a cooling sensation to the sunburned skin, and the indomethacin reduces the inflammation to the skin caused by the sunburn. The composition or mixture of indomethacin and Cetaphil® should be applied to the sunburned areas one to two times daily.

While the invention has been described in connection with what is presently considered to be the most practical and preferred embodiment, it is to be understood that the invention is not to be limited to the disclosed embodiments, but to the contrary, it is intended to cover various modifications and equivalent arrangements included within the spirit and scope of the appended claims. The scope is to be accorded the broadest interpretation so as to encompass all such modifications and equivalent structures as is performed under the law.

What is claimed is:

1. A method for treating sunburned skin, comprising the steps of:

providing a composition which is an admixture consisting essentially of indomethacin and a moisturizing lotion, the moisturizing lotion being an oil and water emulsion consisting essentially of purified water, glycerin, hydrogenated polisobutene, cetearyl alcohol (and) ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium hydroxide, and citric acid having a pH between about 6.3 and 6.5, wherein the indomethacin is maintained in stable and stabilized form in the moisturizing lotion, and wherein the indomethacin is present in a therapeutically effective concentration comprising approximately 100 milligrams of indomethacin for every 30 cc's of moisturizing lotion, applying said mixture topically to sunburned skin and allowing the applied mixture to remain in contact with the skin for an interval sufficient to deliver indomethacin transdermally to the sunburned skin.

2. A composition for treating sunburned skin, consisting of:

a therapeutical amount of indomethacin; and an a moisturizing lotion composition being an oil and water emulsion consisting essentially of purified water, glycerin, hydrogenated polisobutene, cetearyl alcohol (and) ceteareth-20, macadamia nut oil, dimethicone, tocopheryl acetate, stearoxytrimethylsilane (and) stearyl alcohol, panthenol, farnesol, benzyl alcohol, phenoxyethanol, acrylates/C10-30 alkyl acrylate crosspolymer, sodium hydroxide, and citric acid having a pH between about 6.3 and 6.5, wherein the indomethacin is present in stable and stabilized form, wherein said composition contains approximately 100 milligrams of indomethacin for every 30 cc's of moisturizing lotion.

\* \* \* \* \*